United States Patent [19]

Coleman et al.

[11] Patent Number: 4,469,101

[45] Date of Patent: Sep. 4, 1984

[54] SUTURE DEVICE

[75] Inventors: Carl R. Coleman, Powell; Kenneth E. Hughes, Gahanna, both of Ohio

[73] Assignee: Battelle Memorial Institute, Columbus, Ohio

[21] Appl. No.: 385,699

[22] Filed: Jun. 7, 1982

Related U.S. Application Data

[63] Continuation-in-part of Ser. No. 199,715, Oct. 23, 1980, abandoned.

[51] Int. Cl.³ .................. A61B 17/04; A61F 1/00
[52] U.S. Cl. ................................ 128/334 R; 3/1
[58] Field of Search ................ 3/1, 1 B, 1.4; 128/334 R

[56] References Cited

U.S. PATENT DOCUMENTS

| | | | |
|---|---|---|---|
| 2,127,903 | 8/1938 | Bowen | 128/334 R |
| 2,671,444 | 3/1954 | Pease, Jr. | 128/334 R |
| 3,105,492 | 10/1963 | Jeckel | 3/1.4 X |
| 3,124,136 | 3/1964 | Usher | 128/334 R |
| 3,176,316 | 4/1965 | Bodell | 128/334 R X |
| 3,317,924 | 5/1967 | LeVeen et al. | 3/1.4 |
| 3,479,670 | 11/1969 | Medell | 3/1.4 X |
| 3,490,975 | 1/1970 | Lightwood et al. | 3/1.4 X |
| 3,545,008 | 12/1970 | Bader, Jr. | 3/1 |
| 3,613,120 | 10/1971 | McFarland, Jr. | 3/1 |
| 3,938,528 | 2/1976 | Bucalo | 3/1 X |
| 3,993,078 | 11/1976 | Bergentz et al. | 3/1.4 X |
| 4,209,859 | 7/1980 | Hoffman | 3/1 |

Primary Examiner—Ronald L. Frinks
Attorney, Agent, or Firm—Robert B. Watkins

[57] ABSTRACT

A suture device for use in tendon repair which comprises an open network constructed of nontoxic tissue-receptive intersecting members extending between opposite ends and formed to receive and fit tightly over opposing and approximated ends of a lacerated tendon.

7 Claims, 3 Drawing Figures

SUTURE DEVICE

This patent application is a continuation in part of U.S. patent application, Ser. No. 199,715, filed Oct. 23, 1980 now abandoned.

SUMMARY OF THE INVENTION

This invention relates to a tendon repair device used in surgical procedures to repair tendons of living creatures. More particularly it relates to a device which is sutured in place to repair a lacerated tendon.

Briefly and in summary, this invention is a device for use in tendon repair which comprises an open mesh hollow body constructed of nontoxic tissue-receptive intersecting members extending between opposite ends and formed to receive and fit tightly over opposing ends of a lacerated tendon.

Tendon repairs are a difficult medical procedure since tendons are active and moving parts of the anatomy in their normal function. Tendons transmit force, imparting motion to limbs. When a tendon is lacerated and severed, the ends can be sutured together and it will grow together again, although the process is a slow and difficult one. In many situations in the past the part of the limb which is operated by the repaired and healed tendon does not regain the full degree of dexterity and movement previously available.

Various patented approaches and devices have been used and suggested to help solve the problems connected with tendon repair and these have not been entirely satisfactory. Typical examples of prior art patents are the following U.S. Pat. Nos: 2,127,903, 2,671,444, 3,105,492, 3,124,136, 3,613,120, 3,176,316, 3,317,924, 3,479,670, 3,490,975, 3,545,008, 3,993,078, 4,209,859. Their identification is supplied herein in accordance with the duty required of the patent applicant under 37 CFR 1.56.

Even though these prior art patents have taught various suture structures, the current practice for most tendon repair is the use of either the "mattress" type suture or the Bunnell zig-zag type suture in which the stress is placed mainly on the two stitches crossing the tendon laceration and upon one knot. In this practice the ends of the tendon are simply stitched together and the suture tied in a knot.

Another type of suture in current use is the "Mason-Allen" suture in which a suture material is woven in a zig-zag fashion through the tendon and then brought out at the laceration area. This is done both proximally (the side toward the body) and distally (the side toward the extremities) and then the two ends of the sutures are tied to the opposing ends of the other suture. This places the stress again on the knots.

The disadvantage of these practices is that while the tendon is healing for the first three weeks before it has any intrinsic strength, the entire stress is upon the one or two knots of the suture and upon two strands of suture which cross the laceration area.

The current problem of tendon suture technique utilizing the Bunnell or Mason-Allen zig-zag or mattress suture, etc., is that the suture is not strong enough to hold the stress and during healing in about 35% of the cases will: (1) break within the length of the suture, (2) fail at the knot, (3) pull out of the tendon, or (4) develop heavy, short adhesions preventing motion. Joint contracture and/or limited motion of joints occurs due to these failures.

However, it is believed that it is necessary for tendons to heal by adhesions at the site of the laceration since they otherwise derive their main blood supply from only the muscle proximally, and the insertion of the bone distally. But when short adhesions are formed between the tendon sheath and the tendon repair site, or between the phalangeal bones and the tendon repair site, there can be little active motion during the healing process. Without adequate motion during the healing process in many cases the repaired tendon is not considered satisfactory, since the operation of the member is impaired and/or limited in some fashion.

It is an object of this invention that when the device is sutured into place and the repair is completed, limited motion is permissible without pulling the sutures from the tendon, breaking the suture connections or separation of the abutting ends of the tendon. This permits motion of the tendon to occur during the healing process as well as after the healing process. The construction of the device of this invention, by permitting early motion, allows the formation of long thin adhesions rather than short broad ones. This facilitates the motion of the tendon during the healing process and after.

Prior art U.S. Pat. No. 3,176,316-Bodell, shows a prosthetic device structure which is made of woven either Teflon ® or mattress sutures of 4-0 silk. It speaks of other prior art using closely woven or braided Teflon devices coated with liquid Teflon to prevent the growth of tissue. The central portion the Bodell structure is a closely woven shaft. It is stated that the shaft is coated with a solid film of silicone or Teflon in order to provide a still smoother and more impervious outer surface to prevent the growth of scar tissue into the weave shaft.

To the contrary, it is an object of this invention that the structure of the device shall be a predominately open mesh along its entire length so that healing with long adhesions can take place in the open interstices of the device.

It is an object of this invention that the device shall be placed to bring the ends of the lacerated tendon together where the healing process can cause them to grow together, and in the final successful recovery, the natural tendon becomes one continuous length again. At the same time the device is strong enough and secured enough that the device carries the tendon load during movement of the tendon in the healing process.

A further understanding of the invention will be apparent from the following drawings and detailed description.

DETAILED DESCRIPTION OF THE INVENTION

Figure 1:
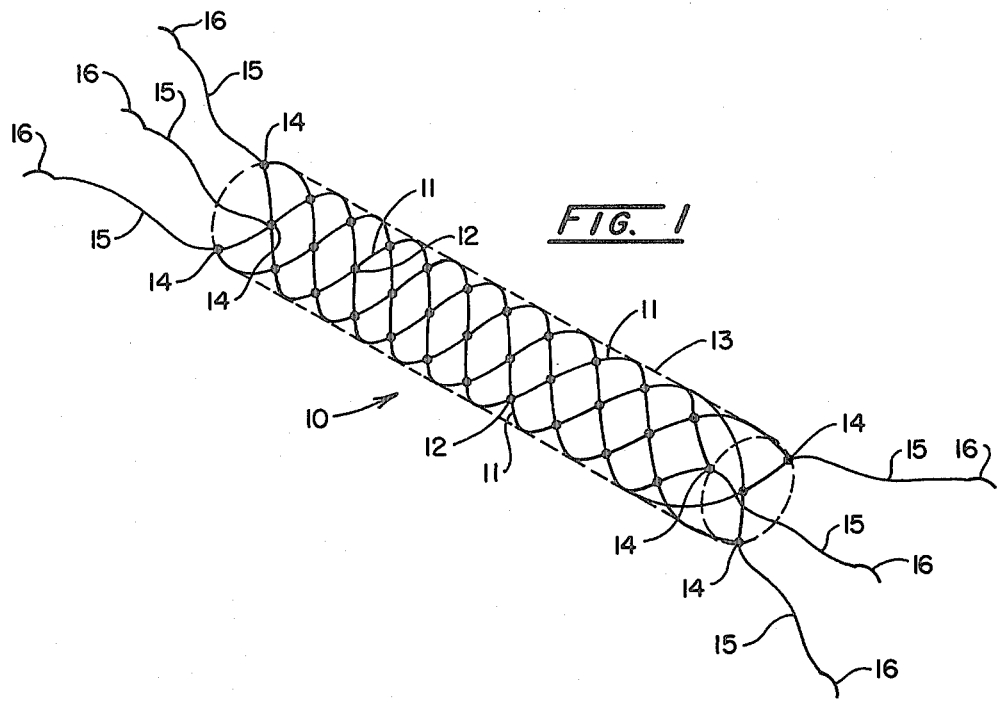
FIG. 1 is a prospective view of the suture device of this invention, including a phantom showing of a mandrel on which the invention device is built and transported.

Referring to FIG. 1, the suture device 10 is constructed of an open mesh of helically formed flexible members 11 which overlap at intersection 12. Typically the members 11 are made from small caliber polyester or other synthetic nonelastic suture material. Their cross sectional diameter may be about 0.08 to 0.25 millimeters.

Because of the flexible nature of the suture device 10, it is preferably constructed on a cylindrical mandrel 13 (shown in phantom in FIG. 1). The mandrel 13 may be allowed to remain within the suture device 10 after construction is complete as a means of support during the packaging and transportation of the product/device to the surgeons who use it. In this event the surgeon removes the mandrel at the time the suture device 10 is applied in the surgical procedures.

An anchor 12 is provided at each intersection of the members 11. The anchors 12 prevent separation of the members 11 so that they remain in contiguous contact. The anchors 12 also prevent longitudinal slippage along a member to a different position. The anchors 12 may be an adhesive droplet, a thermal weld, or they may be in the form of a knot tied during a weaving process of manufacture.

Figure 2:
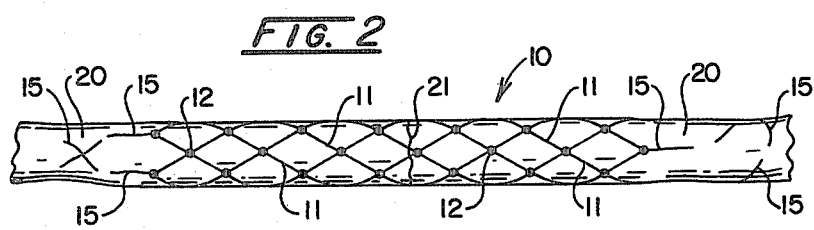
FIG. 2 is an elevational side view of the suture device of this invention in place on a lacerated tendon.
Figure 3:
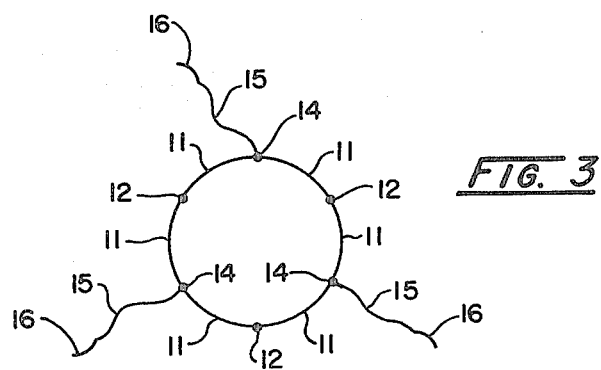
FIG. 3 is an elevational end view of the suture device of this invention.

In the embodiment shown in FIG. 1, there are six helically formed members, three of which are turned in one direction (clockwise) and three of which are turned in the other direction (counter clockwise). At each end, at the intersection, a member 11 having a clockwise turn and a member 11 having a counter clockwise turn meet in an anchor position 14. At each end anchor position 14, one or the other of the members are severed and the other continues as a suture strand 15 for use in anchoring the stuture device 10 to a natural tendon 20, as shown in FIG. 2. A surgical needle 16 is attached to the end of each suture strand 15 for use in the surgical suturing procedures of connecting the suture device 10 securely to the natural tendon 20 or other part of the anatomy. The needle may be attached by swaging its hollow body closed over the suture material.

Referring to FIG. 2, in the surgical procedure of using the suture device 10, a natural tendon 20 having lacerated ends 21 is brought to a position with the ends abutting and approximated with the suture device 10 loosely encircling the joint. By pulling proximally and distally on the suture strands 15 the suture device 10 is caused to tightly grip the tendon and slightly imbed members 11 in the natural tendon 20. Using the needles 16, suture strands 15 are imbedded in the natural tendon 20, looped through, and knotted as necessary to provide a secure attachment with the lacerated ends maintained in position to heal together properly.

Because of the anchors 12 and because of the generally open mesh arrangement, with a relatively long "pitch" of the helices in the suture device 10 structure, a very tight grip on the tendon is obtained for a relatively short longitudinal pull on the suture strands 15. By this means a very tight grip is obtained on the natural tendon 20.

In the suture device 10 of this invention, the mesh of the structure is a relatively "open network". By open is meant that the space between members is large relative to the size of the members. While the exact limits of "openness" for the successful practice of the invention is not known, those skilled in the art will be able to ascertain through experimentation when the structure becomes too closed for success. The mesh must be predominately open to the extent that long thin adhesions can form between the surrounding tissue and the natural tendon within. By predominately, it is meant that the openness of the network is of greater area than the area covered by the members on the projection of tubular form. Example suture devices of the construction of this invention were tested on chickens. It is thought that 80-85% openness may be a threshold range of openness, where the successful benefits of the invention may be realized to some degree. In the successful suture devices, the mesh had an openness such that space between members was at least about 85% of the tubular projection generated by the helices of the suture device. The mesh of the suture device of this invention is predominately open.

EXAMPLE I

A suture device of the following construction was made and tested successfully. The mesh was open enough to allow the development of long adhesions over the members and through the spaces. The device was a multiple wound helix having helices turned in opposite directions on a mandrel (clockwise and counter clockwise). The material was size 6-0 polyester suture strand (2.8 to 3.9 mils diameter). The average suture strand member was 3 mils diameter (0.08 millimeters). The pitch from one position to an equivalent position longitudinally on the next member was 5 millimeters. Thus, each open space was approximately 2×2 millimeters in each direction between the intersection of members The members were anchored to one another by knotting. The degree of "openness" in this example suture device was 92% of the total area covered by the device. When tested it allowed the growth of long adhesions which permitted a good degree of movement in the limbs of the host.

EXAMPLE II

A device was constructed similar to that of Example I except that the device was constructed on a mandrel of 6 mm dia. using 3-0 polyester suture material which has an average diameter of 10 mils (0.25 millimeters). The spacing between members was 6 millimeters longitudinally between the intersection of members. Strands were anchored to one another by knotting. In this device the openness was 89% and the device would be suitable for a larger tendon such as the long flexor tendons in the human ankle or feet.

In the use of this invention the injured limb is temporarily immobilized. The patient is instructed to undertake controlled passive and active motion exercise therapy causing motion of the tendon. This allows the joints to remain mobile and the limbs to move and allows the tendon to heal with long adhesions rather than short adhesions. The long adhesions are formed in the interstices of the prosthetic device. It is necessary for the tendons to heal by adhesions since they derive their predominate blood supply from the muscle proximally and from the insertion of bone distally. The vincula, which are connections between the phalanx and tendon, carry blood supply to the very thin mesotenon.

The members 11 may be of a variety of suitable materials such as Polydek ®, a synthetic suture material manufactured by Deknatel Div. of Howmedica, Inc., Floral Park, N.Y. or Mersilene ®, manufactured by Ethicon, Inc., Somerville, N.J., or other similar synthetic suture material. Members 11 may also be of biodegradeable material such as collagen filament or polyglycolide-polylactide filaments. The material should be strong, flexible and non-toxic. In addition, it should be tissue receptive; i.e., not rejected by living tissue.

The mandrel 13 used in the construction of the suture device device 10 may be any suitable sterilizable material of the proper diameter. It has been found that a semi-rigid Teflon rod makes a good mandrel. When the device is completed on the mandrel, the entire assemblage, including the mandrel, is individually wrapped and sterilized by contact with ethylene oxide gas, steam, dry heat or radiation before delivery.

While the preferred embodiment of this invention shows six helically formed members with three being generated in clockwise rotation and three being generated in counter clockwise rotation, the number of members may be varied depending on the size and kind of tendon for which the device is made. Larger suture devices may be expected to have more members than smaller ones as this would provide greater strength for a natural tendon which is expected to exert more force. At the same time a greater number of members could be used on larger devices without reducing the openness of the mesh which is an important feature of this invention.

It also appears that a mesh of individual diamond shaped opening between members could be built without the use of helically generated member forms since the helically formed continuous members is important only from a construction standpoint. An open mesh hollow body of helices may be constructed in other ways, such as molding, without departing from a recognition of the important features of this invention.

It is herein understood that although the present invention has been specifically disclosed with the preferred embodiments and examples, modification and variations of these concepts herein disclosed may be resorted to by those skilled in the art. Such modifications and variations are considered to be within the scope of the invention and the appended claims.

What is claimed is:

1. A tendon suture device for repair of lacerated tendons by approximating the lacerated ends of the tendon, comprising:
   a. An uncovered open network defining a hollow projection of a tubular form constructed of interconnected oppositely turned helices of non-toxic tissue receptive intersecting flexible non-elastic nonrigid members extending between opposite ends formed to receive opposing and approximated ends of a lacerated tendon, the members being anchored one to another at their ends and at their intersections, the openness of the network being of greater area than the area covered by the members on the projection of tubular form;
   b. the suture being operably strong enough to carry the tendon load when in place on a tendon, with the tendon within the tubular form of the suture device, and with the host tissue surrounding the tendon and suture device, to permit only slight movement between the host tissue surrounding the tendon and relatively no movement between the approximated ends of the lacerated tendon;
   c. the openness being further characterized to permit development of relatively long adhesions between the tendon and the host tissue through the interstices of the open network during the healing process between the ends of the lacerated tendon.

2. A suture device according to claim 1 wherein the openness of said network represents more than about 85% of the tubular projection generated by the said helices.

3. A suture device according to claim 1 wherein the openness of the network is at least about 92%.

4. A suture device according to claim 1 wherein the members are anchored to each other by knotting.

5. A suture device according to claim 1 wherein the members are anchored to each other with adhesives.

6. A suture device according to claim 1 wherein the members are anchored to each other by thermal welding.

7. A suture device according to claim 1 wherein the members are anchored to each other by molded structure.

* * * * *